United States Patent
Cellier et al.

(10) Patent No.: US 6,960,665 B2
(45) Date of Patent: Nov. 1, 2005

(54) PROCESS FOR ARYLATING OR VINYLATING OR ALKYNATING A NUCLEOPHILIC COMPOUND

(75) Inventors: Pascal Philippe Cellier, L'Escale (FR); Henri-Jean Cristau, St Aunes (FR); Jean-Francis Spindler, Lyons (FR); Marc Taillefer, Vailhauques (FR)

(73) Assignee: Rhodia Chimie, Boulogne (FR)

( * ) Notice: Subject to any disclaimer, the term of this patent is extended or adjusted under 35 U.S.C. 154(b) by 0 days.

(21) Appl. No.: 10/159,506

(22) Filed: May 31, 2002

(65) Prior Publication Data

US 2003/0171593 A1 Sep. 11, 2003

(30) Foreign Application Priority Data

Dec. 20, 2001 (FR) .............................................. 01 16547

(51) Int. Cl.⁷ .............................................. C07D 231/10
(52) U.S. Cl. ..................... 548/373.1; 548/577; 568/717
(58) Field of Search ....................................... 548/373.1

(56) References Cited

PUBLICATIONS

Buchwald et al., J. Am. Chem. Soc. (2002) vol. 123, pp. 7727–7729.*

* cited by examiner

*Primary Examiner*—Kamal A. Saeed

(57) ABSTRACT

The present invention concerns a process for arylating or vinylating or alkynating a nucleophilic compound. More particularly, the invention concerns arylating nitrogent-containing organic derivatives. The arylating or vinylating or alkynating process of the invention consists of reacting a nucleophilic compound with a compound carrying a leaving group and is characterized in that the reaction is carried out in the presence of an effective quantity of a catalyst based on a metallic element M selected from groups (VIII), (Ib) and (IIb) of the periodic table and at least one at least bidentate ligand comprising at least two chelating atoms, namely at least one oxygen atom and at least one nitrogen atom.

18 Claims, No Drawings

PROCESS FOR ARYLATING OR VINYLATING OR ALKYNATING A NUCLEOPHILIC COMPOUND

This application claim priority under 35 U.S.C. 119 to patent application 01 16547 filed in France on Dec. 20, 2001.

The present invention relates to a process for arylating or vinylating or alkynating a nucleophilic compound.

More particularly, the invention relates to arylating nitrogen-containing organic derivatives.

Many important compounds exist in the agrochemical and pharmaceutical fields, for example arylhydrazines, which result from arylating a nucleophilic compound by creating a carbon-nitrogen bond.

A conventional arylation method consists of carrying out the Ullmann reaction (Ullmann F. and Kipper H., Ber. Dtsch. Chem. Ges. 1905, 38, 2120–2126), by prolonged heating of the reagents at high temperature, in the presence of catalytic or stoichiometric copper. The reactions are usually limited to using aryl iodides and their yields are reduced by competitive formation of biaryl homocoupling products.

Arylation reactions require a catalyst; a number of types of catalyst have been described.

Palladium was used by Buchwald et al., in particular to carry out indole arylation (Org. Lett. 2000, 2, 1403–1406), in the presence of a base in toluene at 80° C.–100° C. Generally, the yields are satisfactory, but the reaction temperature is still high for this type of palladium-based catalyst.

Copper has also been used (Chiriac et al., Rev. Roum. Chim. 1969, 14, 1263–1267) to carry out arylation of sodium salts and pyrazoles by iodobenzene in the presence of a catalytic quantity of copper under DMF reflux. The conditions described are very severe, the temperature is 153° C. and the reaction period is very long at 30 to 40 hours.

Beletskaya et al. (Tetrahedron Lett. 1998, 39, 5617–5622) proposed a combination of palladium and copper when N-arylating benzotriazole. The presence of copper is indispensable to controlling the selectivity of the reaction. The catalyst is a phase transfer catalyst which is not easy to use on an industrial scale.

International patent WO-A-98/00399 proposes the use of a nickel catalyst, but this has proved to be of little effect when arylating heterocycles such as imidazole.

Chan et al. also described (J. Chem. RES. (S) 2000, 367–369) the arylation of azoles from diaryliodonium salts in the presence of a cobalt catalyst under phase transfer conditions.

Buchwald et al. (J. Am. Chem. Soc. 2001, 123, 7727–7729) recently developed a method for arylating nitrogen-containing nucleophiles catalysed by copper. Its catalytic system, composed of a catalyst that is insensitive to air, cuprous iodide and the trans-1,2-diaminocyclohexane ligand, allows heterocycles such as pyrazoles, indoles, carbazole, pyrrole, indazole, imidazole, phthalazinone and 7-azaindole to be arylated in dioxane at 110° C.

The disadvantage of that process is that the temperature is still high when arylation is carried out by aryl chlorides or even by aryl iodides.

The present invention aims to provide a process that overcomes the disadvantages cited above and which is applicable to a very large number of nucleophiles.

We have now discovered, and this constitutes the subject matter of the present invention, a process for arylating or vinylating or alkynating a nucleophilic compound, consisting of reacting said compound with a compound carrying a leaving group, characterized in that the reaction is carried out in the presence of an effective quantity of a catalyst based on a metallic element M selected from groups (VIII), (Ib) and (IIb) of the periodic table and at least one at least bidentate ligand comprising at least two chelating atoms, namely at least one oxygen atom and at least one nitrogen atom.

Throughout the description of the present invention, the term "arylation" is used in its broad sense since it is envisaged that the compound employed carries a leaving group which is either of the unsaturated aliphatic type, or of the carbocyclic aromatic or heterocyclic type.

The term "nucleophilic compound" means an organic hydrocarbon compound that may be acyclic or cyclic and comprises at least one atom carrying a free electron pair, preferably a nitrogen, oxygen, sulphur or phosphorus atom, or comprises a carbon atom that may donate its electron pair.

As mentioned above, the nucleophilic compound comprises at least one atom carrying a free electron pair, which can be carried by a functional group.

Examples of functional groups comprising said atoms that can be mentioned are:

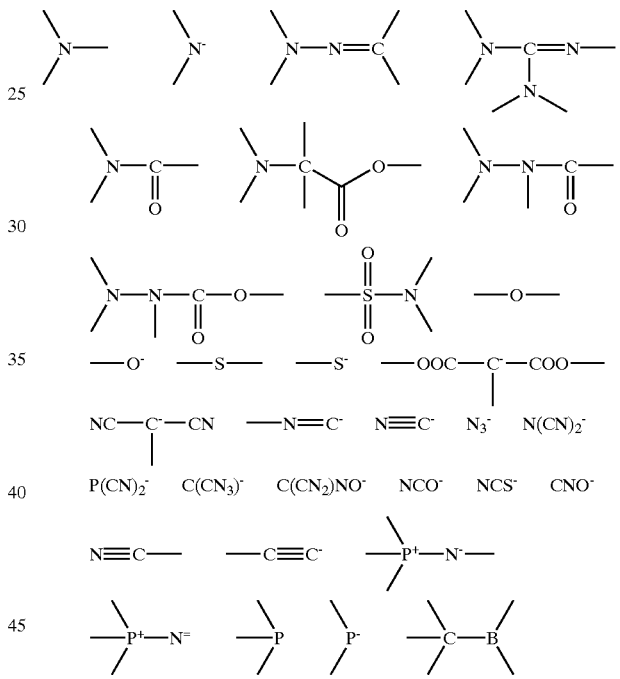

In a further variation of the invention, the nucleophilic compound comprises at least one nitrogen atom carrying a free electron pair included in a saturated, unsaturated or aromatic cycle; the cycle generally contains 3 to 8 atoms.

It should be noted that when the nucleophilic compound comprises a functional group, examples of which were given above, which carries one or more negative charges, said compound is then in its salt form. The counter-ion is generally a metallic cation such as an alkali metal, preferably sodium or lithium or an alkaline-earth metal, preferably calcium, or the residue of an organometallic compound such as a magnesium or zinc compound.

A first advantage of the process of the invention is that it is carried out at moderate temperatures.

A further advantage is that a wide range of arylation agents for nucleophiles can be used, not only aryl iodides, but also aryl bromides.

A still further advantage of the process of the invention is the possibility of using copper rather than palladium as the catalyst, bringing an additional economic advantage.

In accordance with the process of the invention, the catalyst is associated with a ligand which is polydentate, at least bidentate, tridentate or even tetradentate, and which comprises at least two chelating atoms, namely oxygen and nitrogen.

A first category of ligands for carrying out the process of the invention is constituted by oxime, dioxime or hydrazone type ligands.

Oximes

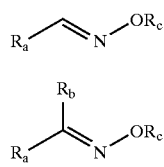

(Ia₁)

(Ia₂)

in which formulae:

at least one of groups $R_a$ and $R_b$ comprises at least one atom of oxygen or a group comprising an oxygen atom;

$R_a$ and $R_b$ independently represent a hydrocarbon group containing 1 to 20 carbon atoms, which may be a linear or branched, saturated or unsaturated acyclic aliphatic group; a monocyclic or polycyclic, saturated, unsaturated or aromatic carbocyclic or heterocyclic group; or a concatenation of said groups;

or $R_a$ and $R_b$ can be bonded to constitute, with the carbon atoms carrying them, a carbocyclic or heterocyclic group containing 3 to 20 monocyclic or polycyclic, saturated, unsaturated, atoms;

$R_c$ represents an alkyl group, preferably $C_1$ to $C_{12}$; an alkenyl or alkynyl group, preferably $C_2$ to $C_{12}$; a cycloalkyl group, preferably $C_3$ to $C_{12}$; or an aryl or arylalkyl group, preferably $C_6$ to $C_{12}$.

As mentioned above, at least one of groups $R_a$ and $R_b$ comprises at least one oxygen atom or a group containing an oxygen atom; examples that can be cited are groups such as hydroxyl, ether, acyl, ester, sulphoxide, sulphone, or phosphine oxide. The OH group is preferred.

In formulae (Ia₁) and (Ia₂), the different symbols can in particular have the meanings given below.

Thus, $R_a$ and $R_b$ can independently represent a linear or branched, saturated or unsaturated, acyclic aliphatic group.

More precisely, $R_a$ and $R_b$ preferably represent a linear or branched, saturated acyclic aliphatic group, preferably $C_1$ to $C_{12}$, and more preferably $C_1$ to $C_4$.

The invention does not exclude the presence of an unsaturated bond on the hydrocarbon chain such as one or more double bonds, which may or may not be conjugated.

The hydrocarbon chain can optionally be interrupted by a heteroatom (for example oxygen, sulphur, nitrogen or phosphorus) or by a functional group provided that it does not react; in particular, a group such as —CO—.

The hydrocarbon chain can optionally carry one or more substituents (for example halogen, ester, amino or alkyl and/or arylphosphine) provided that they do not interfere.

The linear or branched, saturated or unsaturated acyclic aliphatic group can optionally carry a cyclic substituent. The term "cycle" means a saturated, unsaturated or aromatic carbocyclic or heterocyclic cycle.

The acyclic aliphatic group can be connected to the cycle via a covalent bond, a heteroatom or a functional group such as oxy, carbonyl, carboxyl, sulphonyl, etc.

Examples of cyclic substituents that can be envisaged are cycloaliphatic, aromatic or heterocyclic substituents, in particular cycloaliphatic substituents containing 6 carbon atoms in the cycle or benzene, said cyclic substituents themselves optionally carrying any substituent provided that they do not interfere with the reactions occurring in the process of the invention. Particular mention can be made of $C_1$ to $C_4$ alkyl or alkoxy groups.

More particular aliphatic groups carrying a cyclic substituent include cycloalkylalkyl groups, for example cyclohexylalkyl, or arylalkyl groups, preferably $C_7$ to $C_{12}$, in particular benzyl or phenylethyl.

In group formulae (Ia₁) and (Ia₂), groups $R_a$ and $R_b$ can also independently represent a carbocyclic group that is saturated or contains 1 or 2 unsaturated bonds in the cycle, generally $C_3$ to $C_8$, preferably with 6 carbon atoms in the cycle; said cycle can be substituted. A preferred example of this type of group that can be cited is cyclohexyl, optionally substituted with linear or branched alkyl groups containing 1 to 4 carbon atoms.

Groups $R_a$ and $R_b$ can independently represent an aromatic hydrocarbon group, in particular a benzene group with general formula (F₁):

(F₁)

in which:

q represents a whole number from 0 to 5;

Q is a group selected from a linear or branched $C_1$ to $C_6$ alkyl group, a linear or branched $C_1$ to $C_6$ alkoxy group, a linear or branched $C_1$ to $C_6$ alkylthio group, a —NO₂ group, a —CN group, a halogen atom, or a CF₃ group.

$R_a$ and $R_b$ can also independently represent a polycyclic aromatic hydrocarbon group with cycles that can between them form ortho-condensed or ortho- and peri-condensed systems. More particular examples that can be cited is a naphthyl group; said cycle can be substituted.

$R_a$ and $R_b$ can also independently represent a polycyclic hydrocarbon group constituted by at least 2 saturated and/or unsaturated carbocycles or by at least 2 carbocycles only one of which is aromatic and between them forming ortho- or ortho- and peri-condensed systems. Generally, the cycles are $C_3$ to $C_8$, preferably $C_6$. More particular examples that can be cited are the bornyl group and the tetrahydronaphthalene group.

$R_a$ and $R_b$ can also independently represent a saturated, unsaturated or aromatic heterocyclic group in particular containing 5 or 6 atoms in the cycle, including one or two heteroatoms such as nitrogen atoms (not substituted with a hydrogen atom), sulphur or oxygen; the carbon atoms of this heterocycle can also be substituted.

$R_a$ and $R_b$ can also represent a polycyclic heterocyclic group defined as either a group constituted by at least two aromatic or non aromatic heterocycles containing at least one heteroatom in each cycle and between them forming ortho- or ortho- and peri-condensed systems, or a group constituted by at least one aromatic or non aromatic hydrocarbon and at least one aromatic or non aromatic heterocycle forming between them ortho- or ortho- and peri-condensed systems; the carbon atoms of said cycles can optionally be substituted.

Examples of heterocyclic type groups $R_a$ and $R_b$ that can be cited include furyl, thienyl, isoxazolyl, furazannyl, isothiazolyl, pyridyl, pyridazinyl, pyrimidinyl, pyrannyl, phosphino and quinolyl, naphthyridinyl, benzopyrannyl or benzofurannyl groups.

The number of substituents present on each cycle depends on the carbon condensation of the cycle and on the presence or otherwise of an unsaturated bond on the cycle. The maximum number of substituents that can be carried by a cycle can readily be determined by the skilled person.

$R_a$ and $R_b$ can be connected to constitute, with the carbon atoms carrying them, a carbocyclic or heterocyclic group containing 3 to 20 atoms, monocyclic or polycyclic, saturated, unsaturated or aromatic, comprising two or three ortho-condensed cycles which means that at least two cycles have two carbon atoms in common. In the case of polycyclic compounds, the number of atoms in each cycle is preferably in the range 3 to 6. $R_a$ and $R_b$ preferably form a cyclohexane or fluorenone cycle.

In formulae ($Ia_1$) and ($Ia_2$) for oxime type ligands, $R_c$ preferably represents a hydrogen atom or a $C_1$–$C_4$ alkyl group.

Preferred oxime type ligands with formula ($Ia_1$) in which $R_c$ represents a hydrogen atom and $R_a$ represents one of the following groups:

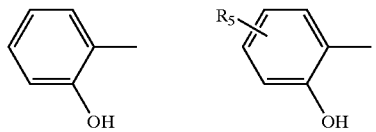

$R_5$ represents an alkyl or alkoxy group, preferably $C_1$ to $C_4$, or an amino group which may or may not be substituted with an alkyl group, preferably $C_1$ to $C_4$.

Examples of preferred ligands are:

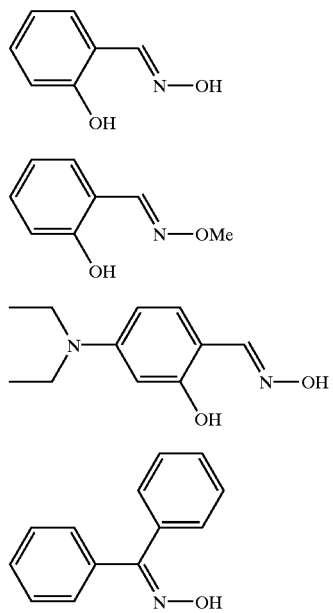

Salox

Salox-Me

4-NEt$_2$-Salox

Benzophenoxime

Ligands with formulae ($Ia_1$) or ($Ia_2$) are known products, as described by Hach, C. C.; Banks, C. V.; Diehl, H.; (Org. Synth.; Coll. Vol. IV; John Wiley & Sons, Inc. 1963, 230–232).

They are obtained by reacting:

an aldehyde or ketone with the following formulae:

($IIa_1$)

ou ($IIa_2$)

in which formulae ($IIa_1$) or ($IIa_2$), $R_a$ and $R_b$ have the meaning given in formulae ($Ia_1$) or ($Ia_2$);

with a hydroxylamine or derivative with formula ($IIa_3$):

($IIa_3$)

in which formula ($IIa_3$), $R_c$ represents a hydrogen atom or has the meaning given in formulae ($Ia_1$) or ($Ia_2$).

Preferred oxime type ligands used in the process of the invention contain an oxygen atom carried by the hydroxyl group of a salicylic aldehyde residue. Preferably, they result from reacting salicylic aldehyde with hydroxylamine or O-methylhydroxylamine.

Dioximes

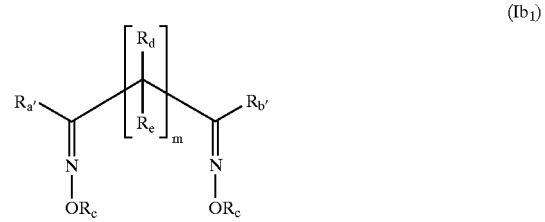

($Ib_1$)

in which formula:

$R_a'$ and $R_b'$, which may be identical or different, have the meanings given in formulae ($Ia_1$) or ($Ia_2$) with the exception of an oxygen atom the presence of which is not obligatory;

$R_a'$ and $R_b'$ can form a carbocyclic or heterocyclic cycle that may or may not be substituted, containing 5 or 6 atoms;

$R_c$ represents an alkyl group, preferably $C_1$ to $C_{12}$; an alkenyl or alkynyl group, preferably $C_2$ to $C_{12}$; a cycloalkyl group, preferably $C_3$ to $C_{12}$; or an aryl or arylalkyl group, preferably $C_6$ to $C_{12}$;

$R_d$, $R_e$, which may be identical or different, represent:
  a hydrogen atom;
  a linear or branched alkyl group containing 1 to 12 carbon atoms, optionally carrying a halogen atom, preferably 1 to 4 carbon atoms, such as methyl, ethyl, propyl, isopropyl, butyl, isobutyl, sec-butyl or tert-butyl;
  a halogen atom;

m equals 0, 1, 2 or 3, preferably 0 or 1.

Preferred dioxime type ligands have formula ($Ib_1$) in which $R_c$ represents a hydrogen atom, m equals 0 and $R_a'$ and $R_b'$ represent a methyl group or form a cyclohexane type cycle.

They are obtained by reacting:

a diketone, preferably an α- or β-diketone with formula:

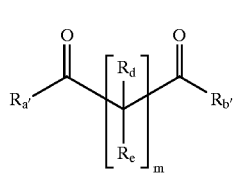
(IIb₁)

in which formula $R_a'$ and $R_b'$, $R_d$ and $R_e$ have the meanings given for formula (Ib₁).

with hydroxylamine or a derivative with formula (IIa₃).

Preferred dioxime type ligands result from reacting 2,3-butanedione or 1,2-cyclohexanedione and hydroxylamine. They have been described by Hach, C. C.; Banks, C. V.; Diehl, H.; (Org. Synth.; Coll. Vol. IV; John Wiley & Sons, Inc. 1963, 230–232).

Examples of preferred ligands are given below:

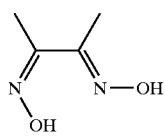  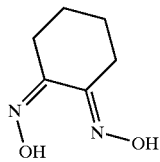

DMG          Nioxime

Hydrazones

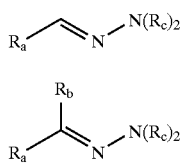
(Ic₁)

(Ic₂)

in which formulae:

$R_a$ and $R_b$, which may be identical or different, have the meanings given in formulae (Ia₁) and (Ia₂);

at least one of groups $R_a$ and $R_b$ comprise at least one oxygen atom or a group containing an oxygen atom;

$R_c$ which may be identical or different, have the meanings given in formulas (Ia₁) and (Ia₂).

Preferred hydrazone type ligands have formulae (Ic₁) or (Ic₂) in which groups $R_c$, which may be identical or different, represent a hydrogen atom or a methyl group, and $R_a$ represents one of the following groups:

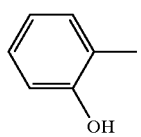  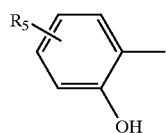

$R_s$ represents an alkyl or alkoxy group, preferably $C_1$ to $C_4$, or an amino group which may or may not be substituted with an alkyl group, preferably $C_1$ to $C_4$.

Hydrazone type ligands result from reacting:

an aldehyde or a ketone with the following formulae:

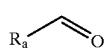
(IIc₁)

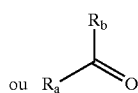
(IIc₂)

ou 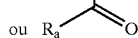

in which formulae (IIc₁) or (IIc₂), $R_a$ and $R_b$ have the meaning given in formulae (Ic₁) or (Ic₂);

with a hydrazine or derivative with formula (IIc₃), preferably O-methylhydroxylamine:

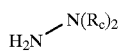
(IIc₃)

in which formula (IIc₃), $R_c$, which may be identical or different, have the meanings given in formulae (Ic₁) or (Ic₂).

Preferred hydrazone type ligands used in the process of the invention contain an oxygen atom carried by the hydroxyl group of a salicylic aldehyde residue. Preferably, they result from reacting salicyclic aldehyde with a hydrazine or an N-substituted or N,N-disubstituted hydrazine, preferably by an alkyl group containing 1 to 4 carbon atoms.

Preferred examples of ligands are:

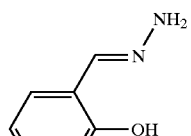

Salzone

Me-salzone

Me₂-salzone

A second category or ligands suitable for use in the invention are tridentate ligands:

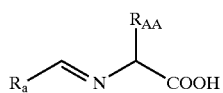
(Id₁)

-continued

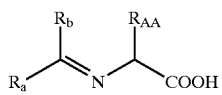
(Id$_2$)

in which formulae:

R$_{AA}$ represent the residue of an amino acid, preferably a hydrogen atom, a linear or branched C$_1$ to C$_{12}$ alkyl group optionally carrying a functional group, or a C$_6$ to C$_{12}$ aryl group or arylalkyl group, preferably a hydroxyl group;

R$_a$ and R$_b$, which may be identical or different, have the meanings given in formulae (Ia$_1$) and (Ia$_2$).

In formulae (Id$_1$) and (Id$_2$), R$_{AA}$ represents an alkyl group that can carry a functional group, examples of which include an —OH, —NH$_2$, —CO—NH$_2$, —NH—C(NH)—NH$_2$ (guanidine), —COOH, —SH, —S—CH$_3$ or an imidazole group.

Preferred tridentate ligands have formulae (Id$_1$) or (Id$_2$) in which R$_{AA}$ represents a hydrogen atom or a methyl group and R$_a$ represents one of the following groups:

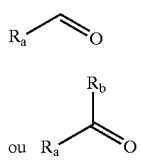

R$_s$ represents an alkyl or alkoxy group, preferably C$_1$ to C$_4$, or an amino group which may or may not be substituted with alkyl groups, preferably C$_1$ to C$_4$.

Ligands with formulae (Id$_1$) and (Id$_2$) result from reacting:

an aldehyde or a ketone with the following formulae:

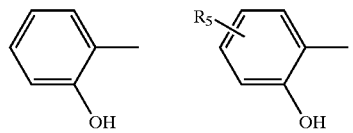
(IIc$_1$)
(IIc$_2$)

in which formulae (IId$_1$) or (IId$_2$), R$_a$ and R$_b$ have the meanings given in formulae (Id$_1$) or (Id$_2$);

with an amino acid, more particularly glycine, cysteine, aspartic acid, glutamic acid or histidine.

The amino acids can be employed in their salt form, preferably in the form of a sodium salt or in the form of a "zwitterion" type ammonium carboxylate.

An example of a preferred ligand is:

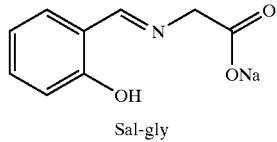

Sal-gly

A third category of ligands that is suitable for carrying out the invention is formed by tetradentate ligands:

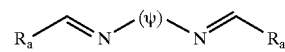
(Ie$_1$)

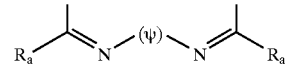
(Ie$_2$)

in which formulae:

R$_a$, which may be identical or different, have the meanings given in formulae (Ia$_1$) and (Ia$_2$);

R$_b$, which may be identical or different, have the meanings given in formulae (Ia$_1$) and (Ia$_2$);

Ψ represents a —HN—CO—NH— group or a skeleton with general formula (F$_2$) or (F$_3$):

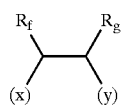
(F$_2$)

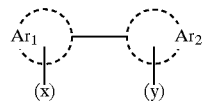
(F$_3$)

in which formulae (F$_2$) and (F$_3$):

R$_f$ and R$_g$ independently represent a hydrocarbon group containing 1 to 20 carbon atoms, which may be a linear or branched, saturated or unsaturated acyclic aliphatic group; a monocyclic or polycyclic, saturated, unsaturated or aromatic carbocyclic or heterocyclic group; or a concatenation of said groups;

or R$_f$ and R$_g$ can be bonded together to constitute, with the carbon atoms carrying them, a carbocyclic or heterocyclic group containing 3 to 20 atoms, which may be saturated, unsaturated, monocyclic or polycyclic;

Ar$_1$ and Ar$_2$ independently represent two substituted or non substituted aromatic, carbocyclic or heterocyclic cycles which may or may not be condensed, which may carry one or more heteroatoms;

x and y respectively represent the two bonds between the skeleton shown as v and the imine groups.

In formulae (Ie$_1$) and (Ie$_2$), symbols R$_a$ and R$_b$ can have the meanings given for formulae (Ia$_1$) and (Ia$_2$).

Preferred tetradentate ligands have formulae (Ie$_1$) or (Ie$_2$) in which R$_b$ represents a hydrogen atom and R$_a$ represents one of the following groups:

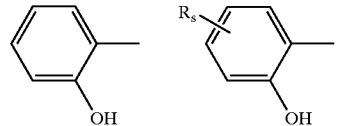

R$_s$ represents an alkyl or alkoxy group, preferably C$_1$ to C$_4$, or an amino group which may or may not be substituted with alkyl groups, preferably C$_1$ to C$_4$.

In formulae (F2) and (F$_3$), symbols R$_f$ and R$_g$ can have the meanings given for R$_a$ and R$_b$ in formulae (Ia$_1$) and (Ia$_2$).

Preferably, R$_f$ is identical to R$_g$.

Further, R$_f$ and R$_g$ can also be bonded together to represent saturated, unsaturated or aromatic monocyclic or polycyclic carbocyclic or heterocyclic groups, preferably bicyclic, which means that at least two cycles have two carbon atoms in common. In the case of polycyclic compounds, the number of carbon atoms in each cycle is preferably in the range 3 to 6.

$R_f$ and $R_g$ can be bonded to constitute, with the carbon atoms carrying them, a saturated or unsaturated, monocyclic or polycyclic carbocyclic or heterocyclic group containing 3 to 20 atoms, preferably a cyclohexane type cycle.

Illustrative examples of groups ψ which can be mentioned are the following cyclic groups:

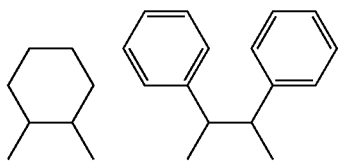

Particularly advantageous compounds have general formula ($F_2$) in which:

$R_f$ and $R_g$ both represent a phenyl or naphthyl group;

$R_f$ and $R_g$ are bonded together to constitute a cycle such as cyclohexane with the carbon atoms carrying them.

In formula ($F_3$), $Ar_1$ and $Ar_2$ together represent an aromatic group which can be a carbocycle containing 6 to 12 carbon atoms or a heterocycle containing 5 to 12 atoms.

In the following description of the present invention, the term "aromatic" designates the conventional idea of aromaticity as defined in the literature, in particular J. March, "Advanced Organic Chemistry", 4$^{th}$ edition, John Wiley & Sons, 1992, pp. 40 ff.

Within the context of the present invention, the aromatic derivative can be monocyclic or polycyclic.

In the case of a monocyclic derivative, it can comprise one or more heteroatoms in its cycle selected from nitrogen, phosphorus, sulphur and oxygen atoms. A preferred mode uses nitrogen atoms not substituted with a hydrogen atom.

Illustrative examples of monocyclic heteroaromatic derivatives that are suitable for use in the present invention that can be cited are pyridine, pyrimidine, pyridazine and pyrazine derivatives.

The carbon atoms of the aromatic derivative can also be substituted. Two neighbouring substituents on the aromatic cycle can also, together with the carbon atoms carrying them, form a hydrocarbon cycle, preferably aromatic, and can if necessary comprise at least one heteroatom. The aromatic derivative is then a polycyclic derivative.

Illustrative examples of this type of compound that can be cited are naphthalene derivatives, quinoline derivatives and isoquinoline derivatives.

Representative examples of compounds with general formula ($F_3$) that can in particular be cited are those in which $Ar_1$ and $Ar_2$ together form either a group deriving from a diphenyl-2,2'-diyl group, or a dinaphthyl-2,2'-diyl group.

The following cyclic groups constitute illustrative examples of groups ψ:

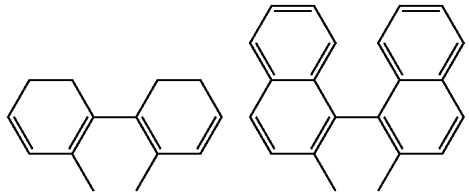

Ligands with formulae ($Ie_1$) or ($Ie_2$) are known products. They are obtained by reacting:
an aldehyde or ketone with the following formulae:

($IIa_1$)

($IIa_2$)

in which formulae ($IIa_1$) or ($IIa_2$), $R_a$ and $R_b$ have the meanings given in formulae ($Ia_1$) or ($Ia_2$);
with a diamine or with formula ($IIe_3$):

($IIe_3$)

in which formula ($IIe_3$), ψ has the meaning given in formulas ($Ie_1$) or ($Ie_2$) and represents a group —HN—CO—NH— or a skeleton with general formula ($F_2$) or ($F_3$).

Preferred tetradentate type ligands used in the process of the invention contain an oxygen atom carried by the hydroxyl group of a salicylic aldehyde residue. They preferably result from reacting salicyclic aldehyde with urea, 1,2-cyclohexanediamine, or 1,2-diphenylethylenediamine.

Examples of preferred ligands are given below:

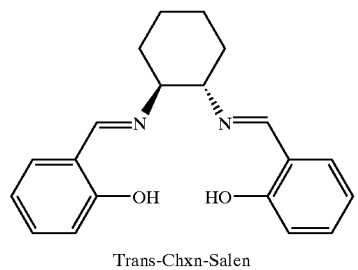

Trans-Chxn-Salen

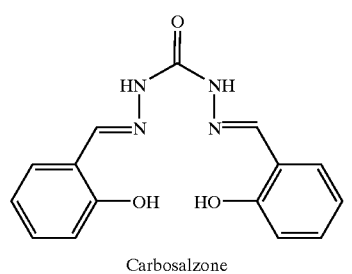

Carbosalzone

Preferred ligands from those cited are those containing a salicyclic aldehyde residue.

More particularly, they are of the oxime or hydrazone type.

The different ligands used in the process of the invention are known products.

Their quantity is a function of the quantity of the metallic element M of the catalyst, preferably copper.

It is generally such that the ratio between the number of moles of ligand and the number of moles of metal is in the range 2 to 1.

It should be noted that the ligand can be introduced concomitantly with the compound supplying the catalytic metallic element. However, the invention also encompasses the case in which a metallic complex is prepared in advance by reacting the compound supplying the catalytic metallic element M and the ligand.

The process of the invention involves a large number of nucleophilic compounds and examples are given below by way of illustration which are not limiting in any way.

A first category of substrates to which the process of the invention is applicable is formed by organic nitrogen-containing derivatives, more particular primary or secondary amines; hydrazine or hydrazone derivatives; amides; sulphonamides; urea derivatives or heterocyclic derivatives, preferably nitrogen-containing and/or sulphur-containing.

More precisely, the primary or secondary amines can be represented by general formula:

$$R_1R_2NH \qquad (IIIa)$$

in which formula (IIIa):

$R_1$, $R_2$, which may be identical or different, represent a hydrogen atom or have the meanings given for $R_a$ and $R_b$ in formula ($Ia_1$) and ($Ia_2$);

at most one of $R_1$ and $R_2$ represent a hydrogen atom.

Preferred amines have formula (IIIa) in which $R_1$, $R_2$, which may be identical or different, represent a $C_1$ to $C_{15}$ alkyl group, preferably $C_1$ to $C_{10}$, a $C_3$ to $C_8$ cycloalkyl group, preferably $C_5$ or $C_6$, or a $C_6$ to $C_{12}$ aryl or arylalkyl group.

More particular examples of groups $R_1$ and $R_2$ that can be mentioned are $C_1$ to $C_4$ alkyl groups, phenyl, naphthyl or benzyl groups.

More specific examples of amines with formula (IIa) that can be mentioned are aniline, N-methylaniline, diphenylamine, benzylamine and dibenzylamine.

It should be noted that the amino group can be in the form of anions. The counter-ion is a metal cation, preferably an alkali metal cation, more preferably sodium or potassium. Examples of such compounds that can be cited are sodium or potassium amide.

Other nucleophilic compounds that can be used in the process of the invention are hydrazine derivatives with formulae (IIIb), (IIIc) or (IIId):

$$NH_2-NH-COOR_3 \qquad (IIIb)$$

$$NH_2-NH-COR_4 \qquad (IIIc)$$

$$NH_2-N=CR_5R_6 \qquad (IIId)$$

In which formulae (IIIb) to (IIId):

$R_3$, $R_4$, $R_5$, $R_6$, which may be identical or different, have the meanings given for $R_1$ and $R_2$ in formula (IIIa).

Groups $R_3$, $R_4$, $R_5$, $R_6$ more particularly represent a $C_1$ to $C_{15}$ alkyl group, preferably $C_1$ to $C_{10}$, a $C_3$ to $C_8$ cycloalkyl group, preferably $C_5$ or $C_6$, or a $C_6$ to $C_{12}$ aryl or aryl alkyl group.

In formulae (IIIb) to (IIId), $R_3$ preferably represents a tertiobutyl group, $R_4$ represents a methyl or phenyl group and $R_5$, $R_6$ represent a phenyl group.

The invention also encompasses amide type compounds, more particularly with formula (IIIe):

$$R_7-NH-CO-R_8 \qquad (IIIe)$$

In which formula (IIIe), $R_7$ and $R_8$ have the meanings given for $R_1$ and $R_2$ in formula (IIIa).

Examples of compounds with formula (IIIe) that can be cited are oxazolidine-2-one, benzamide and acetamide.

The invention is also applicable to sulphonamide type compounds.

They can have the following formula:

$$R_9-SO_2-NH-R_{10} \qquad (IIIf)$$

In which formula (IIIf), $R_9$ and $R_{10}$ have the meanings given for $R_1$ and $R_2$ in formula (IIIa).

An example of a compound with formula (IIIf) that can be cited is tosylhydrazide.

Other types of nucleophilic substrates that can be mentioned are urea derivatives such as guanidines which can be represented by formula (IIIg):

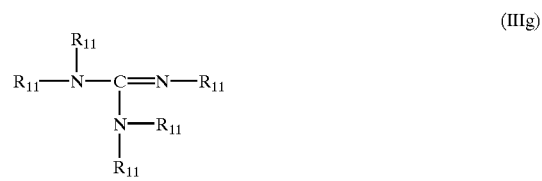

in which formula (IIIg), groups $R_{11}$, which may be identical or different, have the meanings given for $R_1$ and $R_2$ in formula (IIIa).

An example of a compound with formula (IIIg) that can be cited is N,N,N',N'-tetramethylguanidine.

Nucleophilic substrates that are well suited to use in the process of the invention are heterocyclic derivatives comprising at least one nucleophilic atom such as a nitrogen, sulphur or phosphorus atom.

More precisely, they have general formula (IIIh):

in which formula (IIIh):

A represents the residue of a cycle forming all or a portion of a monocyclic or polycyclic, aromatic or non aromatic heterocyclic system wherein one of the carbon atoms is replaced by at least one nucleophilic atom such as a nitrogen, sulphur or phosphorus atom;

$R_{12}$, which may be identical or different, represent substituents on the cycle;

n represents the number of substituents on the cycle.

The invention is applicable to monocyclic heterocyclic compounds with formula (IIIh) in which A represents a saturated or unsaturated or aromatic heterocycle in particular containing 5 or 6 atoms in the cycle and possibly containing 1 or 3 heteroatoms such as nitrogen, sulphur or oxygen, at least one of which is a nucleophilic atom such as NH or S.

A can also represent a polycyclic heterocyclic compound defined as being constituted by at least 2 aromatic or non aromatic heterocycles containing at least one heteroatom in each cycle and forming ortho- or ortho- and pericondensed systems between them, or a group constituted by at least one aromatic or non aromatic carbocycle and at least one aromatic or non aromatic heterocycle forming ortho- or ortho- and peri-condensed systems between them.

It is also possible to start from a substrate resulting from a concatenation of a saturated, unsaturated or aromatic heterocycle as described above and a saturated, unsaturated or aromatic carbocycle. The term "carbocycle" preferably means a cycloaliphatic or aromatic cycle containing 3 to 8 carbon atoms, preferably 6.

It should be noted that the carbon atoms of the heterocycle can optionally be substituted with groups $R_{12}$, either completely or partially.

The number of substituents present on the cycle depends on the number of atoms in the cycle and on the presence or otherwise of unsaturated bonds on the cycle.

The maximum number of substituents that can be carried by the cycle can readily be determined by the skilled person.

In formula (IIIh), n is a number equal to 4 or less, preferably 0 or 1.

Examples of substituents are given below, but this list is not limiting in nature.

Group or groups $R_{12}$, which may be identical or different, preferably represent one of the following groups:

- a linear or branched $C_1$ to $C_6$ alkyl group, preferably $C_1$ to $C_4$ carbon atoms, such as methyl, ethyl, propyl, isopropyl, butyl, isobutyl, sec-butyl or tert-butyl;
- a linear or branched $C_2$ to $C_6$ alkenyl or alkynyl group, preferably $C_2$ to $C_4$, such as vinyl or allyl;
- a linear or branched $C_1$ to $C_6$ alkoxy or thioether group, preferably $C_1$ to $C_4$ such as methoxy, ethoxy, propoxy, isopropoxy or butoxy, or an alkenyloxy group, preferably an allyloxy or phenoxy group;
- a cyclohexyl, phenyl or benzyl group;
- a group or function such as: hydroxyl, thiol, carboxyl, ester, amide, formyl, acyl, aroyl, amide, urea, isocyanate, thioisocyanate, nitrile, nitride, nitro, sulphone, sulphonic, halogen, pseudohalogen or trifluoromethyl.

The present invention is particularly applicable to compounds with formula (IIIh) in which groups $R_{12}$ more particularly represent an alkyl or alkoxy group.

More particularly, optionally substituted residue A represents one of the following cycles:

- a monocyclic heterocycle containing one or more heteroatoms:

- a bicycle comprising a carbocycle and a heterocycle comprising one or more heteroatoms;

- a tricycle comprising at least one carbocycle or a heterocycle comprising one or more heteroatoms;

Preferred examples of heterocyclic compounds are those with formula (IIIh) in which A represents a cycle such as: imidazole, pyrazole, triazole, pyrazine, oxadiazole, oxazole, tetrazole, indole, pyrole, phthalazine, pyridazine or oxazolidine.

Nucleophilic compounds that can also be used in the process of the invention that can be cited are alcohol or thiol type compounds represented by the following formula:

$$R_{13}\text{-}Z \qquad \text{(IIIi)}$$

In which formula (IIIi):

$R_{13}$ represents a hydrocarbon group containing 1 to 20 atoms and has the meanings given for $R_1$ or $R_2$ in formula (IIIa);

Z represents a $OM_1$ or $SM_1$ type group in which $M_1$ represents a hydrogen atom or a metallic cation, preferably an alkali metal cation.

Preferred compounds have formula (IIIi) in which $R_{13}$ represents a hydrocarbon group containing 1 to 20 carbon atoms, which may be a linear or branched, saturated or unsaturated acyclic aliphatic group; a monocyclic or polycyclic, saturated, unsaturated or aromatic carbocyclic or heterocyclic group; or a concatenation of said groups.

More precisely, $R_{13}$ preferably represents a linear or branched saturated acyclic aliphatic group preferably containing 1 to 12 carbon atoms, more preferably 1 to 4 carbon atoms.

The invention also encompasses the presence of an unsaturated bond in the hydrocarbon chain such as one or more double bonds, which may or may not be conjugated, or a triple bond.

As mentioned for $R_a$ defined in formula ($Ia_1$) or ($Ia_2$), the hydrocarbon chain can optionally be interrupted by a heteroatom or a functional group, or it may carry one or more substituents.

In formula (IIIi), $R_{13}$ can also represent a saturated or non saturated carbocyclic group, preferably containing 5 or 6 carbon atoms in the cycle; a saturated or non saturated heterocyclic group, containing 5 or 6 carbon atoms in the cycle including 1 or 2 heteroatoms such as nitrogen, sulphur, oxygen or phosphorus atoms; a monocyclic, aromatic heterocyclic carbocyclic group, preferably phenyl, pyridyl, furyl, pyrannyl, thiophenyl, thienyl, phospholyl, pyrazolyl or imidazolyl, pyrolyl, or a polycyclic, aromatic heterocyclic carbocyclic group which may or may not be condensed, preferably naphthyl.

When $R_{13}$ includes a cycle, it can also be substituted. The nature of the substituent is unimportant provided that it does not interfere with the principal reaction. The number of substituents is generally at most 4 per cycle, usually 1 or 2. Reference should be made to the definition of $R_{12}$ in formula (IIIh).

The invention also encompasses the case in which $R_{13}$ comprises a concatenation of aliphatic and/or cyclic, carbocyclic and/or heterocyclic groups.

One acyclic aliphatic group may be connected to a cycle via a covalent bond, a heteroatom or a functional group such as oxy, carbonyl, carboxy, sulphonyl, etc.

More particular groups are cycloalkylalkyl, for example cyclohexylalkyl, or aralkyl groups containing 7 to 12 carbon atoms, in particular benzyl or phenylethyl.

The invention also encompasses a concatenation of carbocyclic and/or heterocyclic groups, more particularly a concatenation of phenyl groups separated by a covalent bond or an atom or a functional group G such as: oxygen, sulphur, sulpho, sulphonyl, carbonyl, carbonyloxy, imino, carbonylimino, hydrazo or alkylene ($C_1$–$C_{10}$, preferably $C_1$)-diimino.

The linear or branched, saturated or unsaturated acyclic aliphatic group can optionally carry a cyclic substituent. The term "cycle" means a saturated, unsaturated or aromatic carbocyclic or heterocyclic cycle.

Preferred compounds with formula (IIIi) have general formula (IIIi$_1$):

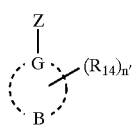

in which:
B represents the residue of a monocyclic or polycyclic, aromatic, carbocyclic group or a divalent group constituted by a concatenation of two or more monocyclic aromatic carbocyclic groups;

$R_{14}$ represents one or more substituents, which may be identical or different;

Z represents an $OM_1$ or $SM_1$ group in which $M_1$ represents a hydrogen atom or a metallic cation, preferably an alkali metal cation;

n' is 5 or less.

Examples of substituents $R_{14}$ can be found by referring to those for $R_{12}$ defined for formula (IIIh).

More particular compounds with formula (IIIi$_1$) are those in which the residue (B) represents:

a monocyclic or polycyclic aromatic carbocyclic group with cycles that can together form an ortho-condensed system with formula (F$_4$):

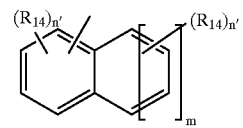

in which formula (F$_4$), m represents 0, 1 or 2 and symbols $R_{14}$ and n', which may be identical or different, have the meanings given above;

a group constituted by a concatenation of two or more monocyclic aromatic carbocyclic groups with formula (F$_5$):

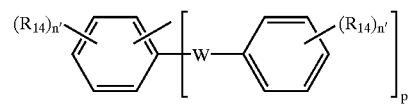

in which formula (F$_5$), symbols $R_{14}$ and n', which may be identical or different, have the meanings given above, p is 0, 1, 2 or 3 and w represents a covalent bond, an alkylene or alkylidene $C_1$ to $C_4$ group, preferably a methylene group or isopropylidene group, or a functional group such as G.

Preferred compounds with formula (IIIi) have formulae (F$_4$) and (F$_5$) in which:

$R_{14}$ represents a hydrogen atom, a hydroxyl group, a —CHO group, a —NO$_2$ group, or a linear or branched alkyl or alkoxy group containing 1 to 6 carbon atoms, preferably 1 to 4 carbon atoms, more preferably methyl, ethyl, methoxy or ethoxy;

w represents a covalent bond, an alkylene or alkylidene group containing 1 to 4 carbon atoms or an oxygen atom;

m is 0 or 1;

n' is 0, 1 or 2;

p is 0 or 1.

Illustrative examples of compounds with formula (IIIi) that can in particular be mentioned are:

those in which residue B has formula (F$_4$) in which m and n' equal 0, such as phenol or thiophenol;

those in which residue B has formula (F$_4$) in which m equals 0 and n' equals 1, such as hydroquinone, pyrocatechine, resorcin, alkylphenols, alkylthiophenols, alkoxyphenols, salicylic aldehyde, p-hydroxybenzaldehyde, methyl salicylate, p-hydroxybenzoic acid methyl ester, chlorophenols, nitrophenols or p-acetamidophenol;

those in which residue B has formula (F$_4$) in which m equals 0 and n' equals 2, such as dialkylphenols, vanillin, isovanillin, 2-hydroxy-5-acetamidobenzaldehyde, 2-hydroxy-5-propionamidobenzaldehyde, 4-allyloxybenzaldehyde, dichlorophenols, methylhydroquinone or chlorohydroquinone;

those in which residue B has formula (F$_4$) in which m equals 0 and n' equals 3, such as 4-bromovanillin, 4-hydroxyvanillin, trialkylphenols, 2,4,6-trinitrophenol, 2,6-dichloro-4-nitrophenol, trichlorophenols, dichlorohydroquinones or 3,5-dimethoxy-4-benzaldehyde;

those in which residue B has formula (F$_4$) in which m equals 1 and n' is 1 or more, such as dihydroxynaphthalene, 4-methoxy-1-naphthol or 6-bromo-2-naphthol;

those in which residue B has formula (F₅) in which p is 1 and n' is 1 or more, such as 2-phenoxyphenol, 3-phenoxyphenol, phenylhydroquinone, 4,4'-dihydroxybiphenyl, isopropylidene 4,4'-diphenol (bisphenol A), bis(4-hydroxyphenyl)methane, bis(4-hydroxyphenyl)sulphone, bis(4-hydroxyphenyl) sulphoxide or tetrabromo bisphenol A.

Other nucleophilic compounds that can be used in the process of the invention are hydrocarbon derivatives containing a nucleophilic carbon.

More particular examples are malonate type anions comprising a —OOC—HC⁻—COO— group.

Alkyl malonate anions with formula (IIIj) can be mentioned:

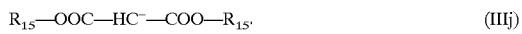
R₁₅—OOC—HC⁻—COO—R₁₅'.      (IIIj)

In which formula (IIIj), $R_{15}$ and $R_{15}'$, which may be identical or different, represent an alkyl group containing 1 to 12 atoms in the alkyl group, preferably 1 to 4 atoms.

It is also possible to cite malodinitrile type anions containing a NC—HC⁻—CN group.

It is also possible to use nitrile type compounds represented by formula (IIIk):

R₁₆—CN      (IIIk)

in which formula $R_{16}$ has any nature and has the meanings given for $R_1$ and also represents a metallic cation, preferably an alkali cation, more preferably lithium, sodium or potassium.

$R_{16}$ has the meanings given for $R_1$.

Examples of nitrites that can be mentioned are acetonitrile, cyanobenzene optionally carrying one or more substituents on the benzene ring, or ethanal cyanhydrine CH₃CH(OH)CN.

It is also possible to use acetylenide type compounds in the process of the invention.

They can be represented by the formula (IIIm):

R₁₇—C≡⁻      (IIIm)

in which formula $R_{17}$ is of any nature and the counter-ion is a metal cation, preferably a sodium or potassium atom.

$R_{17}$ has the meanings given for $R_1$.

Particular examples that can be cited are sodium or potassium acetylide or diacetylide.

Other classes of nucleophilic compounds that can be employed in the process of the invention that can be cited are profene type compounds and their derivatives represented by the following formula:

R₁₈—HC⁻—COO—R₁₉      (IIIn)

in which formula:

$R_{18}$ has the meanings given for $R_1$;

$R_{19}$ represents an alkyl group containing 1 to 12 atoms in the alkyl group, preferably 1 to 4 atoms.

Preferred compounds are those with formula (IIIn) in which $R_{18}$ represents an alkyl group containing 1 to 12 carbon atoms, a cycloalkyl group containing 5 or 6 carbon atoms and an aryl group containing 6 or 12 carbon atoms or a nitrogen-containing heterocycle containing 5 or 6 atoms.

A further category of nucleophiles that can be used in the process of the invention is formed by amino acids and their derivatives:

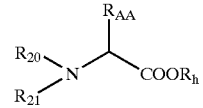
(IIIo)

in this formula:

$R_{AA}$ represents the residue of an amino acid, preferably a hydrogen atom, a linear or branched $C_1$ to $C_{12}$ alkyl group optionally carrying a functional group, an aryl group or an arylalkyl $C_6$ to $C_{12}$ group or a functional group, preferably a hydroxyl group;

$R_{20}$ and $R_{21}$ have the meanings given for $R_1$ and $R_2$ in formula (IIIa);

$R_h$ represents a hydrogen atom, a metal cation, preferably an alkali metal cation or a hydrocarbon group containing 1 to 12 carbon atoms, preferably a $C_1$ to $C_{12}$ alkyl group.

In formula (IIIo), $R_{AA}$ represents an alkyl group that can carry a functional group, examples of which that can be cited being an —OH, —NH₂, —CO—NH₂, —NH—CNH—, —HN—C(O)—NH₂—, —COOH, —SH, —S—CH₃ group or an imidazole, pyrole or pyrazole group.

Examples of amino acids that can be cited are glycine, cysteine, aspartic acid, glutamic acid and histidine.

Examples of nucleophilic compounds of any other nature that can be mentioned are phosphorus or phosphorus- and nitrogen-containing compounds, more particularly those with the following formulae:

phosphides with formula (R₂₂)₂—P⁻ (IIIp)

phosphines with formula (R₂₂)₃—P⁻ (IIIq)

phosphonium diazoylides with formula (R₂₂)₃—P⁺—N²⁻ (IIIr)

phosphonium azoylides with formula (R₂₂)₃—P⁺—N⁻R₂₃ (IIIs)

in which formulae (IIIp) to (IIIs), groups $R_{22}$, which may be identical or different, and group $R_{23}$ represent:

an alkyl group containing 1 to 12 carbon atoms;

a cycloalkyl group containing 5 or 6 carbon atoms;

a cycloalkyl group containing 5 or 6 carbon atoms, substituted with one or more alkyl radicals containing 1 to 4 carbon atoms, or alkoxy radicals containing 1 or 4 carbon atoms;

a phenylalkyl group the aliphatic portion of which contains 1 to 6 carbon atoms;

a phenyl group;

a phenyl substituted with one or more alkyl radicals containing 1 to 4 carbon atoms or alkoxy containing 1 to 4 carbon atoms or one or more halogen atoms.

More particular examples of phosphorus-containing compounds that can be cited are tricyclohexylphosphine, trimethylphosphine, triethylphosphine, tri-n-butylphosphine, triisobutylphosphine, tri-tert-butylphosphine, tribenzylphosphine, dicyclohexylphenylphosphine, triphenylphosphine, dimethylphenylphosphine, diethylphenylphosphine and di-tert-butylphenylphosphine.

Other nucleophilic compounds that can be used include boronic acids or their derivatives, more particularly those with the following formula:

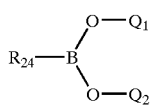

in which:
R$_{24}$ represents a monocyclic or polycyclic, aromatic, carbocyclic or heterocyclic group;
Q$_1$, Q$_2$, which may be identical of different, represent a hydrogen atom, a linear or branched, saturated or unsaturated aliphatic group containing 1 to 20 carbon atoms, or a R$_{24}$ group.

More precisely, the boronic acid has formula (IIIt) in which group R$_{24}$ represents an aromatic carbocyclic or heterocylic group. R$_{24}$ can have the meanings given above for B in formula (IIIi$_1$). However, R$_{24}$ more particularly represents a carbocyclic group such as a phenyl, naphthyl or heterocyclic group such as a pyrrolyl, pyridyl, pyrimidyl, pyridazinyl, pyrazinyl, 1,3-thiazolyl, 1,3,4-thiadiazolyl or a thienyl group.

The aromatic cycle can also be substituted. The number of substituents is generally at most 4 per cycle, but usually it is 1 or 2. Reference should be made to the definition of R$_{12}$ in formula (IIIh) for examples of substituents.

Preferred substituents are alkyl or alkoxy groups containing 1 to 4 carbon atoms, an amino group, a nitro group, a cyano group, a halogen atom or a trifluoromethyl group.

Q$_1$, Q$_2$, which may be identical or different, more particularly represent a hydrogen atom, or a linear or branched acyclic aliphatic group containing 1 to 20 carbon atoms which may be saturated or contain one or more unsaturated bonds in the chain, preferably 1 to 3 unsaturated bonds, preferably simple or conjugated double bonds.

Q$_1$, Q$_2$, preferably represent an alkyl group containing 1 to 10 carbon atoms, preferably 1 to 4, or an alkenyl group containing 2 to 10 carbon atoms, preferably a vinyl or a 1-methylvinyl group.

Q$_1$, Q$_2$, can have the meanings given for R$_{24}$; in particular, any cycle can also carry a substituent as described above.

Preferably, R$_{24}$ represents a phenyl group.

The scope of the present invention encompasses derivatives of boronic acids such as anhydrides and esters, more particularly alkyl esters containing 1 to 4 carbon atoms.

Particular examples of arylboronic acids that can be cited are: benzeneboronic acid, 2-thiopheneboronic acid; 3-thiopheneboronic acid; 4-methylbenzeneboronic acid, 3-methylthiophene-2-boronic acid, 3-aminobenzeneboronic acid, 3-arninobenzeneboronic acid hemisulphate, 3-fluorobenzeneboronic acid, 4-fluorobenzeneboronic acid, 2-formylbenzeneboronic acid, 3-formylbenzeneboronic acid, 4-formylbenzeneboronic acid, 2-methoxybenzeneboronic acid, 3-methoxybenzeneboronic acid, 4-methoxybenzeneboronic acid, 4-chlorobenzeneboronic acid, 5-chlorothiophene-2-boronic acid, benzo[b]furan-2-boronic acid, 4-carboxybenzeneboronic acid, 2,4,6-trimethylbenzeneboronic acid, 3-nitrobenzeneboronic acid, 4-(methylthio)benzeneboronic acid, 1-naphthaleneboronic acid, 2-naphthaleneboronic acid, 2-methoxy-1-naphthaleneboronic acid, 3-chloro-4-fluorobenzeneboronic acid, 3-acetamidobenzeneboronic acid, 3-trifluoromethylbenzeneboronic acid, 4-trifluoromethylbenzeneboronic acid, 2,4-dichlorobenzeneboronic acid, 3,5-dichlorobenzeneboronic acid, 3,5-bis(trifluoromethyl)benzeneboronic acid, 4,4'-biphenyldiboronic acid, and esters and anhydrides of said acids.

The present text provides lists of nucleophilic compounds that are in no way limiting and any type of nucleophilic compound can be envisaged.

In accordance with the process of the invention, a —C—C or —C—Nu—(O, S, P, N, Si, B . . . ) bond can be created by reacting a nucleophilic compound with a compound comprising an unsaturated bond in the position α to the leaving group.

More precisely, it is a compound comprising a leaving group Y represented by the formula (IV):

$$R_0\text{—}Y \qquad (IV)$$

in which formula R$_0$ represents a hydrocarbon group containing 2 to 20 carbon atoms and has a double bond or a triple bond located in the position α to a leaving group Y, or a monocyclic or polycyclic, aromatic, carbocyclic and/or heterocyclic group.

In accordance with the process of the invention, the compound with formula (III) is reacted with a compound with formula (IV) in which:
R$_0$ represents an aliphatic hydrocarbon group containing a double bond or a triple bond in the position α to the leaving group or a cyclic hydrocarbon group containing an unsaturated bond carrying a leaving group;
R$_0$ represents a monocyclic or polycyclic, aromatic, carbocyclic and/or heterocyclic group;
Y represents a leaving group, preferably a halogen atom or a sulphonic ester group with formula —OSO$_2$—R$_e$, in which R$_e$ is a hydrocarbon group.

The compound with formula (IV) will henceforth be designated as a "compound carrying a leaving group".

In the formula for the sulphonic ester group, R$_e$ is a hydrocarbon group of any nature. However, given that Y is a leaving group, it is advantageous from an economic viewpoint for R$_e$ to be simple in nature, and more particularly to represent a linear or branched alkyl group containing 1 to 4 carbon atoms, preferably a methyl or ethyl group, but it can also represent a phenyl or tolyl group or a trifluoromethyl group, for example. The preferred group Y is a triflate group, which corresponds to a group R$_e$ representing a trifluoromethyl group.

Bromine or chlorine atoms constitute preferred leaving groups.

More particularly, compounds with formula (IV) used in accordance with the process of the invention can be classified into three groups:

(1) aliphatic type compounds, carrying a double bond which can be represented by formula (IVa):

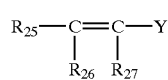

in which formula (IVa):
R$_{25}$, R$_{26}$ and R$_{27}$, which may be identical or different, represent a hydrogen atom or a hydrocarbon group containing 1 to 20 carbon atoms, which can be a linear or branched, saturated or unsaturated aliphatic group; a monocyclic or polycyclic, saturated, unsaturated or aromatic carbocyclic or heterocyclic group; or a concatenation of aliphatic and/or carbocyclic and/or heterocyclic groups as defined above;
Y represents the leaving group, as defined above;

(2) aliphatic type compounds, carrying a triple bond, represented by formula (IVb):

$$R_{25}-C\equiv C-Y \qquad (IVb)$$

in which formula (IVb):
R$_{25}$ has the meaning given in formula (IVa);
Y represents a leaving group as defined above;
(3) aromatic type compounds, hereinafter designated as a "halogenoaromatic compound" and which can be represented by formula (IVc):

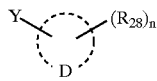
(IVc)

in which:
D represents the residue of a cycle forming all or a portion of a monocyclic or polycyclic, aromatic, carbocyclic and/or heterocyclic system;
R$_{28}$, which may be identical or different, represent substituents on the cycle;
Y represents a leaving group as defined above;
n" represents the number of substituents on the cycle.

The invention is applicable to unsaturated compounds with formulae (IVa) and (IVb) in which R$_{25}$ preferably represents a saturated linear or branched acyclic aliphatic group preferably containing 1 to 12 carbon atoms.

The invention does not exclude the presence of a further unsaturated bond on the hydrocarbon chain, such as a further triple bond or one or more double bonds, which may or may not be conjugated.

The hydrocarbon chain can optionally be interrupted by a heteroatom (for example oxygen or sulphur) or by a functional group provided that it does not react; in particular, a group such as —CO— can be cited.

The hydrocarbon chain can optionally carry one or more substituents provided that they do not react under the reaction conditions; particular mention can be made of a halogen atom, a nitrile group or a trifluoromethyl group.

The linear or branched, saturated or unsaturated acyclic aliphatic group can optionally carry a cyclic substituent. The term "cycle" means a saturated, unsaturated or aromatic, carbocyclic or heterocyclic cycle.

The acyclic aliphatic group can be connected to the cycle via a covalent bond, a heteroatom or a functional group such as oxy, carbonyl, carboxy, sulphonyl, etc.

Examples of cyclic substituents that can be envisaged are cycloaliphatic, aromatic or heterocyclic substituents, in particular cycloaliphatic, containing 6 carbon atoms in the cycle, or benzenic, said cyclic substituents themselves optionally carrying any substituent provided that they do not interfere with the reactions occurring in the process of the invention. Particular mention can be made of alkyl or alkoxy groups containing 1 to 4 carbon atoms.

More particular examples of aliphatic groups carrying a cyclic substituent are aralkyl groups containing 7 to 12 carbon atoms, in particular benzyl or phenylethyl.

In formulae (IVa) and (IVb), R$_{25}$ can also represent a carbocyclic group that may or may not be saturated, preferably containing 5 or 6 carbon atoms in the cycle, preferably cyclohexyl; a heterocyclic group, which may or may not be saturated, in particular containing 5 or 6 carbon atoms in the cycle 1 or 2 of which are heteroatoms such as nitrogen, sulphur or oxygen; a monocyclic aromatic carbocyclic group, preferably phenyl, or a polycyclic aromatic carbocyclic group, which may or may not be condensed, preferably naphthyl.

Regarding R$_{26}$ and R$_{27}$, they preferably represent a hydrogen atom or an alkyl group containing 1 to 12 carbon atoms, or a phenyl group or an aralkyl group containing 7 to 12 carbon atoms, preferably a benzyl group.

In formulae (IVa) and/or (IVb), R$_{25}$, R$_{26}$ and R$_{27}$ more particularly represent a hydrogen atom or R$_{25}$ represents a phenyl group and R$_{26}$, R$_{27}$ represent a hydrogen atom.

Examples of compounds with formulae (IVa) and (IVb) that can be cited are vinyl chloride or bromide, β-bromo- or β-chlorostyrene or bromoalkyne or iodoalkyne.

The invention is of particular application to halogenoaromatic compounds with formula (IVc) in which D is the residue of a cyclic compound, preferably containing at least 4 carbon atoms in its cycle, preferably 5 or 6, optionally substituted, and representing at least one of the following cycles:
a monocyclic or polycyclic aromatic carbocycle, i.e., a compound constituted by at least 2 aromatic carbocycles and between them forming ortho- or ortho- and peri-condensed systems, or a compound constituted by at least 2 carbocycles only one of which is aromatic and between them forming ortho- or ortho- and peri-condensed systems;
a monocyclic aromatic heterocycle containing at least one of heteroatoms P, O, N or S or a particle aromatic heterocycle, i.e., a compound constituted by at least 2 heterocycles containing at least one heteroatom in each cycle wherein at least one of the two cycles is aromatic and between them forming ortho- or ortho- and peri-condensed systems, or a compound constituted by at least one carbocycle and at least one heterocycle at least one of the cycles being aromatic and forming between them ortho- or ortho- and peri-condensed systems.

More particularly, optionally substituted residue D preferably represents the residue of an aromatic carbocycle such as benzene, an aromatic bicycle containing two aromatic carbocycles such as naphthalene; or a partially aromatic bicycle containing two carbocycles one of which is aromatic, such as tetrahydro-1,2,3,4-naphthalene.

The invention also envisages the fact that D can represent the residue of a heterocycle provided that it is more electrophilic than the compound with formula (IIIh).

Particular examples that can be cited are an aromatic heterocycle such as furan or pyridine; an aromatic bicycle comprising an aromatic carbocycle and an aromatic heterocycle such as benzofuran or benzopyridine; a partially aromatic bicycle comprising an aromatic carbocycle and a heterocycle such as methylenedioxybenzene; an aromatic bicycle comprising two aromatic heterocycles such as 1,8-naphthylpyridine; a partially aromatic bicycle comprising a carbocycle and an aromatic heterocycle such as 5,6,7,8-tetrahydroquinoline.

In the process of the invention, a halogenoaromatic compound with formula (IVc) is preferably used in which D represents an aromatic nucleus, preferably a benzene or naphthalene nucleus.

The aromatic compound with formula (IVc) can carry one or more substituents.

In the present text, the term "several" generally means less than 4 substituents R$_{28}$ on the aromatic nucleus.

Reference should be made to the definitions of R$_{12}$ in formula (IIIh) for examples of substituents.

In formula (IVc), n" is a number that is 4 or less, preferably 1 or 2.

Examples of compounds with formula (IVc) that can be cited are p-chlorotoluene, p-bromoanisole and p-bromotrifluorobenzene.

The quantity of compound carrying a leaving group with formula (IV), preferably with formula (IVa) or (IVb) or (IVc), is generally expressed as the ratio of the quantity of nucleophilic compound close to stoichiometry. The ratio between the number of moles of compound carrying a leaving group and the number of moles of nucleophilic compound is usually in the range 0.9 to 1.2.

In accordance with the process of the invention, the nucleophilic compound preferably with formulae (IIIa) to (IIIt) is reacted with a compound carrying a leaving group with formula (IV), preferably with formula (IVa) or (IVb) or (IVc) in the presence of an effective quantity of a catalyst based on a metallic element M selected from group (VIII), (Ib) and (IIb) and a ligand as defined in the invention.

In the present text, reference will be made below to the periodic table published in the Bulletin de la Société Chimique de France, n° 1 (2366).

The different metals M can be used as a mixture, in particular as a mixture with copper.

Examples of metals M that can be cited are copper, silver, palladium, cobalt, nickel, iron and/or zinc.

When a single metal M is used, copper or palladium are preferably selected.

Examples of catalysts that can be used that can be cited are copper metal or organic or inorganic compounds of copper (I) or copper (II).

The catalysts employed in the process of the invention are known products.

Examples of copper catalysts of the invention that can be cited are cuprous bromide, cupric bromide, cuprous iodide, cupric iodide, cupric chloride, basic copper (II) carbonate, cuprous nitrate, cupric nitrate, cuprous sulphate, cupric sulphate, cuprous sulphite, cuprous oxide, cuprous acetate, cupric acetate, cupric trifluoromethylsulphonate, cupric hydroxide, copper (I) methylate, copper (II) methyate and chlorocupric methylate with formula $ClCuOCH_3$.

A palladium catalyst is used in the process of the invention. The palladium can be supplied in the form of a finely divided metal or in the form of an inorganic derivative such as an oxide or hydroxide. It is possible to use a mineral salt, preferably a nitrate, sulphate, oxysulphate, halide, oxyhalide, silicate, carbonate, or an organic derivative, preferably the cyanide, oxalate or acetylacetonate; an alcoholate, more preferably methylate or ethylate; a carboxylate, still more preferably the acetate. It is also possible to use complexes, in particular chlorine-containing or cyanide containing complexes with palladium and/or alkali metals, preferably sodium, potassium or ammonium.

Examples of compounds that can be used to prepare the catalysts of the invention that can be cited are palladium (II) bromide, palladium (II) chloride, palladium (II) iodide, palladium (II) cyanide, hydrated palladium (II) nitrate, palladium (II) oxide, dihydrated palladium (II) sulphate, palladium (II) acetate, palladium (II) propionate, palladium (II) butyrate, palladium (II) benzoate, palladium (II) acetylacetonate, ammonium tetrachloropalladate (II), potassium hexachloropalladate (IV), palladium (II) tetramine nitrate, palladium (II) dichlorobis(acetonitrile), palladium (II) dichlorobis(benzonitrile), palladium (II) dichloro(1,5-cyclooctadiene), palladium (II) dichlorodiamine, palladium (0) tetrakistriphenylphosphine, palladium (II) acetate and trisbenzylideneacetone palladium (0).

Specific examples of nickel derivatives that can be cited are nickel (II) halides such as nickel (II) chloride, bromide or iodide; nickel (II) sulphate; nickel (II) carbonate; salts of organic acids containing 1 to 18 carbon atoms, in particular the acetate or propionate; nickel (II) complexes such as nickel (II) acetylacetonate, nickel (II) dibromo-bis-(triphenylphosphine), nickel (II) dibromo-bis(pyridine); or nickel (0) complexes such as nickel (0) bis-(cycloocta-1,5-diene) or nickel (0) bis-diphenylphosphinoethane.

It is also possible to use catalysts based on iron or zinc, generally in the form of the oxide, hydroxide or salts such as halides, preferably the chloride, nitrate or sulphate.

Preferably, cupric chloride or bromide and cuprous oxide are selected.

The quantity of catalyst used, expressed as the mole ratio between the number of moles of catalyst and the number of moles of compound with formula (IV) is generally in the range 0.01 to 0.1.

A base, the function of which is to trap the leaving group, is also used in the process of the invention.

The feature of the base is that it has a pKa of 2 or more, preferably in the range 4 to 30.

The pKa is defined as the ionic dissociation constant of the acid/base pair when water is used as the solvent.

Reference should be made, inter alia, to the "Handbook of Chemistry and Physics", 66$^{th}$ edition, p. D-161 and D-162 in order to select a base with a suitable pKa.

Suitable bases that can be cited include mineral bases such as alkali metal carbonates, bicarbonates or hydroxides, preferably of sodium, potassium, caesium or alkaline-earth metals, preferably calcium, barium or magnesium.

It is also possible to use alkali metal hydrides, preferably sodium hydride or alkali metal alcoholates, preferably of sodium or potassium, more preferably sodium methylate, ethylate or tertiobutylate.

It is also possible to use organic bases as tertiary amines, more particularly triethylamine, tri-n-propylamine, tri-n-butylamine, methyldibutylamine, methyldicyclohexylamine, ethyldiisopropylamine, N,N-diethylcyclohexylamine, pyridine, dimethylamino-4-pyridine, N-methylpiperidine, N-ethylpiperidine, N-n-butylpiperidine, 1,2-methylpiperidine, N-methylpyrrolidine and 1,2-dimethylpyrrolidine.

Preferred bases are alkali metal carbonates.

The quantity of base employed is such that the ratio between the number of moles of base and the number of moles of aromatic compound carrying the leaving group is preferably in the range 1 to 4.

The arylation or vinylation or alkynylation reaction of the invention is usually carried out in the presence of an organic solvent.

An organic solvent is used that does not react under the reaction conditions.

The type of solvent used is preferably a polar organic solvent, more preferably aprotic:

linear or cyclic carboxamides such as N,N-dimethylacetamide (DMAC), N,N-diethylacetamide, dimethylformamide (DMF), diethylformamide or 1-methyl-2-pyrrolidinone (NMP);

dimethylsulphoxide (DMSO);

hexamethylphosphotriamide (HMPT);

tetramethyurea;

nitrated compounds such as nitromethane, nitroethane, 1-nitropropane, 2-nitropropane or mixtures thereof, and nitrobenzene;

aliphatic or aromatic nitriles such as acetonitrile, propionitrile, butanenitrile, isobutanenitrile, pentanenitrile, 2-methylglutaronitrile or adiponitrile;

tetramethylene sulphone (sulpholane);

organic carbonates such as dimethylcarbonate, diisopropylcarbonate or di-n-butylcarbonate;

alkyl esters such as ethyl or isopropyl acetate;

halogenated or non halogenated aromatic hydrocarbons such as chlorobenzene or toluene;

ketones, such as acetone, methylethylketone, methylisobutylketone, cyclopentanone, cyclohexanone;

nitrogen-containing heterocycles such as pyridine, picoline and quinolines.

It is also possible to use a mixture of solvents.

The quantity of organic solvent to be used is determined as a function of the nature of the selected organic solvent.

It is determined so that the concentration of the compound carrying a leaving group in the organic solvent is preferably in the range 5% to 40% by weight.

The arylation or vinylation or alkynylation reaction of the nucleophilic compound takes place at a temperature that is advantageously in the range 0° C. to 120° C., preferably in the range 20° C. to 100° C., more preferably in the range 25° C. to 85° C.

The arylation or vinylation or alkynylation reaction is generally carried out at atmospheric pressure, but higher pressures of up to 10 bars, for example, can also be used.

In practice, the reaction is simple to carry out.

The order of using the reagents is not critical. Preferably, the (preferably copper) catalyst, the ligand, the nucleophilic compound with formula (III), the base, the compound carrying a leaving group with formula (IV) and the organic solvent are charged.

The reaction medium is heated to the desired temperature.

The progress of the reaction is monitored by following the disappearance of the compound carrying a leaving group.

At the end of the reaction, a product of the type R-Nu-$R_0$ is obtained, more particularly an arylated compound comprising the residue of the nucleophilic compound and the residue of an electrophilic compound preferably with the following formula (V):

(V)

in which formula (V), D, R, $R_{28}$, Nu and n" have the meanings given above.

The compound obtained is recovered using conventional techniques, in particular by crystallisation from an organic solvent.

More specific examples of organic solvents that can be mentioned are aliphatic or aromatic, halogenated or non halogenated hydrocarbons, carboxamides and nitriles. Particular mention can be made of cyclohexane, toluene, dimethylformamide and acetonitrile.

Examples of the invention will now be given. These examples are given by way of illustration and are not limiting in nature.

Before describing the examples, we shall describe the operating protocol used in all of the examples unless otherwise indicated. The preparation of certain ligands and catalysts is also illustrate.

In the examples, the degree of transformation (TT) corresponds to the ratio between the number of moles of substrate transformed and the number of moles of substrate engaged.

The yield (RR) corresponds to the ratio between the number of moles of product formed and the number of moles of substrate engaged.

EXAMPLES

Operating Protocol

The following are successively introduced into a 35 ml Schlenk tube placed in a nitrogen atmosphere:

copper catalyst (0.05 mmoles);

ligand (0.1 mmoles);

nucleophilic compound (0.75 mmoles);

a base (1 mmoles);

56 μl of iodobenzene (0.5 mmoles);

and 300 μl of acetonitrile.

The mixture is placed in an oil bath at a temperature of 50° C. and stirred for 90 hours.

After this period, a sample of reaction medium is removed and filtered over celite (or filter medium) eluting with ether or dichloromethane depending on the solubility. The arylated compound obtained is extracted with ethyl ether or dichloromethane, then distilled water and the product obtained is analysed by gas chromatography using 1,3-dimethoxybenzene as an internal reference.

Preparation of Ligands:

a—Preparation of Salox:

The ligand was prepared using the operating mode described by Hach, C. C.; Banks, C. V.; Diehl, H.; (Org. Synth.; Coll. Vol. IV; John Wiley & Sons, Inc. 1963, 230–232).

A solution of 13.51 g of potassium hydroxide (240.8 mmoles) in 30 ml of distilled water cooled in an ice bath was added to a solution of 16.73 g of hydroxylamine hydrochloride (240.8 mmoles) dissolved in 30 ml of distilled water also cooled in an ice bath.

The mixture was stirred for 20 minutes at 0° C. then 9.5 ml of salicylaldehyde (89.2 mmoles) was slowly added. Stirring was continued for 30 minutes at 0° C. then three hours at 100° C.

The reaction mixture was then placed in the refrigerator to precipitate a brown solid isolated by filtration through a frit, washed with copious amounts of water and then with petroleum ether, then dried in a dessiccator.

The salicylaldozime was purified by re-crystallisation from a petroleum ether/chloroform mixture.

9.91 g of white-orange crystals were obtained, which corresponded to a 81% yield.

The characteristics were as follows:

M.Pt: 57.5° C. (petroleum ether/CHCl$_3$) (Lit: 57° C.: Holly, F. W.; Cope. A. C.; J. Am. Chem. Soc. 1944, 66, 1875–1879);

$^1$H NMR/DMSO-d$_6$: δ 11.34 (wide sulphur, 1H, OH oxime), 10.11 (wide s, 1H, phenolic OH), 8.36 (s, 1H, H$_7$), 7.47 (m, 1H, H$_6$), 7.21 (m, 1H, H$_4$), 6.81–6.91 (m, 2H, H$_{3,5}$).

$^{13}$C NMR/DMSO-d$_6$: δ 156.02 (C2), 147.92 (C7), 130.37 (C4), 128.07 (C6), 119.27 (C5), 118.12 (C1), 115.97 (C3).

b—Preparation of nioxime (cyclohexane-1,2-dionedioxime):

The ligand was prepared using the operating mode described by Hach, C. C.; Banks, C. V.; Diehl, H.; (Org. Synth.; Coll. Vol. IV; John Wiley & Sons, Inc. 1963, 230–232).

A solution of 13.51 g of potassium hydroxide (240.8 mmoles) in 50 ml of distilled water cooled in an ice bath was added to a solution of 16.73 g of hydroxylamine hydrochloride (240.8 mmoles) dissolved in 50 ml of distilled water also cooled in an ice bath.

The mixture was stirred for 20 minutes at 0° C. then 10 g of molten cyclohexane-1,2-dione (89.2 mmoles) was slowly added.

Stirring was continued for 30 minutes at 0° C. then for three hours at 100° C.

The reaction mixture was then placed in the refrigerator for a few hours to precipitate an egg-yellow solid isolated by filtration through a frit, washed with copious amounts of water and then with petroleum ether then dried in a dessiccator.

The nioxime was purified by re-crystallisation from a 98/2 acetone/water mixture.

6.10 g of white crystals were obtained, which corresponded to a 48% yield.

The characteristics were as follows:

M.Pt: 193–194° C. (acetone/water) (Lit: 193–196° C., dioxane: Bischoff, C.; Ohme, R.; J. Prakt. Chem. 1973, 315, 505–509);

$^1$H NMR/DMSO-$d_6$: δ 11.07 (wide s, 2H, OH), 2.48 (m, 4H, $H_{2,5}$), 1.55 (m, 4H, $H_{3,4}$).

$^{13}$C NMR/DMSO-$d_6$: δ 151.89 (C1 and C6), 24.68 (C2 and C5), 21.82 (C3 and C4).

Preparation of Catalysts:

The catalysts used were commercially available products with the exception of activated Cu (A) and activated Cu (B). An operating mode is also provided for preparing said catalysts, which were then used in the examples.

a—Activated Cu (A) prepared by purification of metallic copper:

A few grams of copper powder were ground for 15 minutes in a solution composed of 2 g of iodine dissolved in 100 ml of acetone.

The mixture was filtered through a frit, washed with 150 ml of a solution composed of concentrated hydrochloric acid (75 ml) and acetone (75 ml), using 100 ml of acetonitrile then 100 ml of acetone.

Elimination of all of the cuprous iodide was ensured by washing with acetonitrile, a solvent in which it is highly soluble (27.51 g/l).

The activated copper was dried in a vacuum dessiccator in the presence of $P_2O_5$.

It was used immediately after its preparation.

b—Activated Cu (B) prepared by reduction of copper sulphate:

30 g of copper sulphate pentahydrate (120 mmoles) was dissolved in a solution composed of 100 ml of distilled water and 5 ml of hydrochloric acid.

1.96 g of zinc (30 mmoles) was slowly added to this solution, taking care that the temperature did not exceed 40° C.

The precipitated copper was isolated by filtering through a frit, washed with distilled water then with acetone and dried in a dessiccator in the presence of $P_2O_5$.

It was used after preparation.

Examples 1 to 8

Comparative Example a

In this series of tests, pyrazole was arylated with bromobenzene in the presence of different copper catalysts: activated Cu (A), activated Cu (B), CuI, CuBr, $Cu_2O$, CuO, $CuBr_2$.

Pyrazole (51 mg) was arylated with bromobenzene (53 μl; 0.5 mmoles), in the presence of caesium carbonate (325.8 mg; 1 mmole) and copper catalysts: activated Cu (A) (3.17 mg; 0.05 mmoles), activated Cu (B) (3.17 mg; 0.05 mmoles); CuI (9.52 mg; 0.05 mmoles); CuBr (7.17 mg; 0.05 mmoles); $Cu_2O$ (7.15 mg; 0.05 mmoles); CuO (3.97 mg; 0.05 mmoles); $CuBr_2$ (11.17 mg; 0.05 mmoles).

The quantity of ligand represented two molar equivalents with respect to copper.

The acetonitrile was employed in a quantity such that the concentration of the bromobenzene was 1.67 M.

The reaction was carried out at 50° C. for 90 hours.

The different copper catalysts were employed in the arylation reaction of the invention in the presence of ligands as defined in the invention and mentioned in table (I).

By way of comparison, the same reaction was carried out but using 1,10-phenanthroline as the ligand.

The yields of 1-phenyl-1H-pyrazole determined after 24 hours of reaction in the examples of the invention and in the comparative example, are shown in table (I):

TABLE I

| Ex. Ref | Ligand/[Cu] | Ligand quantity (mg) | Activated Cu (A) | Activated Cu (B) | CuI | CuBr | $Cu_2O$ | CuO | $CuBr_2$ |
|---|---|---|---|---|---|---|---|---|---|
| 1 | DMG | 11.6 | 58.5% | 52.7% | 7.4% | 40.6% | 11.3% | | |
| 2 | 2-Py-Aldox | 12.2 | 23.9% | 31.0% | 41.1% | 52.7% | 57.1% | 57.7% | 50.5% |
| 3 | Nioxime | 14.2 | 25.0% | 16.8% | | | | | |
| 4 | Salox | 13.7 | | | | | 64.2% | 48.5% | |
| 5 | ChXn-Salen | 32 | | | | | 1.8% | | |
| 6 | 5-MeO-salox | 16.7 | | | | | 69.8% | | |
| 7 | Carbosalzone | 29.6 | | | | | 24.9% | | |
| 8 | 4-$Net_2$-Salox | 20.8 | | | | | 50.7% | | |
| a | 1,10-Phen | 18 | 22.3% | | | 13.3% | | 0% | |

Example 9

Example 1 was repeated, replacing the bromobenzene with iodobenzene.

The catalyst was activated Cu (A) in an amount of 10%.

The yield of 1-phenyl-1H-pyrazole obtained was 100%.

Example 10

Example 2 was repeated, replacing the bromobenzene with iodobenzene.

The catalyst was cuprous oxide in an amount of 5%.

The reaction was carried out at 20° C.

The yield of 1-phenyl-1H-pyrazole obtained was 80%.

Examples 11 to 15

In this series of examples, pyrazole (51 mg) and bromobenzene (53 μl; 0.5 mmoles) were reacted in the presence of cuprous oxide (3.57 mg; 0.025 mmoles, 5%), Salox (20%) and caesium carbonate and different solvents as listed in Table (II).

The acetonitrile was used in a quantity such that the concentration of the bromobenzene was 1.67 M.

The reaction was carried out at 82° C. over 24 hours.

The yields of 1-phenyl-1H-pyrazole obtained are shown in Table (II):

TABLE II

| Ex. Ref. | Solvent | Yield (%) |
| --- | --- | --- |
| 11 | Acetonitrile | 84.3 |
| 12 | Dimethylformamide | 74.8 |
| 13 | 2-methylglutaronitrile | 52.3 |
| 14 | Adiponitrile | 51.1 |
| 15 | Toluene | 12.7 |

Examples 16 to 20

In the following examples, pyrazole (51 mg) and bromobenzene were reacted in the presence of cuprous oxide (5%), a Salox, DMG or 2-Py-Aldox ligand (20%) and caesium carbonate or potassium tertiobutylate (112 mg/1 mmole) in the presence of acetonitrile.

The acetonitrile was used in a quantity such that the concentration of the bromobenzene was 1.67 M.

The reaction was carried out at 82° C. over 24 hours.

The yields of 1-phenyl-1H-pyrazole obtained are shown in Table (II):

TABLE III

| Ex. Ref. | Base | Ligand | Yield (%) |
| --- | --- | --- | --- |
| 16 | $Cs_2CO_3$ | Salox | 84.3 |
| 17 | $Cs_2CO_3$ | DMG | 83.6 |
| 18 | $Cs_2CO_3$ | 2-Py-Aldox | 80.7 |
| 19 | KOt-Bu | Salox | 0.7 |
| 20 | KOt-Bu | 2-Py-Aldox | 19.5 |

Examples 21 to 33

In the following examples, pyrazole (51 mg) and bromobenzene were reacted in the presence of different copper catalysts, different ligands (20%) and caesium carbonate (2 equivalents) in the presence of acetonitrile.

The acetonitrile was used in a quantity such that the concentration of the bromobenzene was 1.67 M.

The reaction was carried out at 82° C. over 24 hours.

The yields of 1-phenyl-1H-pyrazole obtained are shown in Table (IV):

TABLE IV

| Ex. Ref | Ligand/[Cu] | Quantity ligand (mg) | $Cu_2O$ | CuBr | CuI |
| --- | --- | --- | --- | --- | --- |
| 21 | 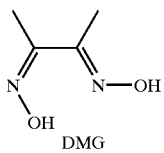 DMG | | 83.6% | 82.5% | 75.9% |
| 22 | 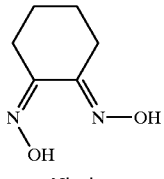 Nioxime | | 84.2% | 78.1% | 82.5% |
| 24 | 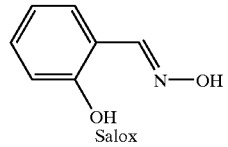 Salox | | 84.3% | 83.6% | 84.2% |
| 25 |  5-MeO-Salox | | 91.5% | 85.2% | |

TABLE IV-continued

| Ex. Ref | Ligand/[Cu] | Quantity ligand (mg) | Cu$_2$O | CuBr | CuI |
|---|---|---|---|---|---|
| 26 | -Net$_2$-Salox | 4 | 76.8% | 55.6% | |
| 27 | Me$_2$-salzone | 16.4 | 61.0% | 54.1% | |
| 28 | Me-salzone | 15 | 84.1% | 78.3% | |
| 29 | Salzone | 13.6 | 83.5% | | |
| 30 | Sal-gly | 19.7 | 88.4% | 79.2% | |
| 31 | Chxn-Salen | 32.2 | 80.5% | 60.9% | |

TABLE IV-continued

| Ex. Ref | Ligand/[Cu] | Quantity ligand (mg) | Cu₂O | CuBr | CuI |
|---|---|---|---|---|---|
| 32 | Carbosalzone | | 87.0% | 73.2% | |

Examples 34 to 36

In the following examples, pyrazole (51 mg) was reacted with the different substituted aryl bromides shown in Table (V) in the presence of cuprous oxide (5%), Salox (20%) and caesium carbonate (2 equivalents) in the presence of acetonitrile.

The acetonitrile was used in a quantity such that the concentration of the bromobenzene was 1.67 M.

The reaction was carried out at 82° C. over 24 hours.

The yields of the different arylpyrazoles obtained are shown in Table (V):

Examples 37 to 39

In the following examples, the different pyrazoles shown in Table (V) were reacted with bromobenzene in the presence of cuprous oxide (5%), Salox (20%) and caesium carbonate (2 equivalents) in the presence of acetonitrile.

The reaction was carried out at 82° C. over 24 hours.

The yields of the different arylpyrazoles obtained are shown in Table (VI):

TABLE V

| Ex. Ref | Aryl bromide | Bromide quantity (mg) | Product obtained | Yield (%) | Selectivity (%) |
|---|---|---|---|---|---|
| 34 | F₃C—⟨⟩—Br | 112.5 | F₃C—⟨⟩—N-pyrazole | 79.1% | 96.3% |
| 35 | NC—⟨⟩—Br | 91 | NC—⟨⟩—N-pyrazole | 81.4% | 89.2% |
| 36 | MeO—⟨⟩—Br | 93.5 | MeO—⟨⟩—N-pyrazole | 73.3% | 95.8% |

TABLE VI

| Ex. Ref | Starting pyrazole | Pyrazole quantity (mg) | Product obtained | Yield (%) | Selectivity (%) |
|---|---|---|---|---|---|
| 37 | pyrazole-H | 51 mg | N-phenylpyrazole | 86.7% | 100% |

TABLE VI-continued

| Ex. Ref | Starting pyrazole | Pyrazole quantity (mg) | Product obtained | Yield (%) | Selectivity (%) |
|---|---|---|---|---|---|
| 38 | F$_3$C-pyrazole (NH) | 102 mg | F$_3$C-pyrazole (N-Ph) | 38.9% | 100% |
| 39 | 3-methylpyrazole (NH) | 61.5 mg | mixture of 1-Ph-3-methyl and 1-Ph-5-methyl pyrazoles | 25%* | 100% |

*Mixture of two isomers in an approximate ratio of 4/1.

Examples 40 to 42

In the following examples, imidazole (51 mg) and iodobenzene were reacted in the presence of cuprous oxide (5%), the different ligands shown in Table (VII) (20%) and caesium carbonate (2 equivalents) in the presence of acetonitrile.

The temperature and reaction period are shown in Table (VII).

The yield of N-phenylimidazole obtained is shown in Table (VII):

TABLE VII

| Ex. Ref | Ligand | Temperature, °C. | Period (h) | Yield (%) | Selectivity (%) |
|---|---|---|---|---|---|
| 40 | Salox | 82 | 24 | 97 | 97 |
| 41 | 2-Py-Aldox | 82 | 24 | 93 | 93 |
| 42 | Salox | 50 | 48 | 100 | 100 |

Examples 43 to 46

In the following examples, imidazole (51 mg) and bromobenzene were reacted in the presence of cuprous oxide (5%), the different ligands shown in Table (VII) (20%) and caesium carbonate (2 equivalents) in the presence of acetonitrile.

The temperature was 82° C. and the reaction period was 24 hours.

The yield of N-phenylimidazole obtained is shown in Table (VIII):

TABLE VIII

| Ex. Ref. | Ligand | Yield (%) | Selectivity (%) |
|---|---|---|---|
| 43 | Carbosalozone | 55.0 | 99.6 |
| 44 | Sal-gly | 48.8 | 100 |
| 45 | Salzone | 47.9 | 100 |

Example 46

The nitrogen α to the oxygen of t-butyl carbazate (99 mg) was arylated.

To this end, t-butyl carbazate (H$_2$N—NH-Boc) was reacted with iodobenzene in the presence of CuBr, caesium carbonate and DMG (dimethylgloxime).

The reaction was carried out in acetonitrile.

N(α)-phenyltertiobutylcarbazate was obtained in a yield of 33% after 24 hours at 82° C.

Example 47

Piperidine (56 mg; 0.75 mmoles) was arylated by reacting it with iodobenzene in the presence of cuprous oxide (3.6 mg; 0.025 mmoles, 5%), a Salox ligand (20%), and caesium carbonate (0.325 g, 1 mmole, 2 equivalents) in the presence of acetonitrile.

The temperature was 82° C. and the reaction period was 24 hours.

N-phenylpiperidine was obtained in a yield of 17.7%.

Example 48

4-t-butylphenol (112.5 mg; 0.75 mmoles) was arylated by reacting it with iodobenzene in the presence of cuprous oxide (5%), a Salox ligand (20%) and caesium carbonate in the presence of acetonitrile.

150 mg of 3 Å sieve was added to the reaction medium at the start of the reaction.

The temperature was 82° C. and the reaction period was 24 hours.

The 4-t-butylphenyl ether was obtained in a yield of 80.5%.

Example 49

Oxazolidin-2-one (65.3 mg) was arylated by reacting it with iodobenzene in the presence of cuprous oxide, a Salox ligand and caesium carbonate in the presence of acetonitrile.

The temperature was 82° C. and the reaction period was 24 hours.

The corresponding 3-phenyloxazolidin-2-one was obtained in a yield of 54.2%.

Example 50

Indole (87.9 mg, 0.75 mmoles) was arylated by reacting it with iodobenzene in the presence of cuprous oxide, a Salox ligand and caesium carbonate in the presence of acetonitrile.

The temperature was 82° C. and the reaction period was 24 hours.

The corresponding N-phenylindole was obtained in a yield of 82.2%.

Example 51

Benzophenone hydrazone (147.2 mg) was arylated with iodobenzene.

The temperature was 82° C. and the reaction period was 24 hours.

The corresponding N-phenylhydrazone was obtained in a yield of 82.2%.

What is claimed is:

1. A process for arylating, vinylating or alkynating a nucleophilic compound, comprising the step of reacting said nucleophilic compound which is a pyrazole with a compound carrying a leaving group, wherein the reaction is carried out in the presence of a catalytically effective amount of a catalyst comprising:

a metallic element M selected from the group consisting of the elements of the groups (VIII), (Ib) and (IIb) of the periodic table, and at least one at least bi-dentate ligand, comprising at least two chelating atoms, namely at least one oxygen atom and at least one nitrogen atom of the following formulae $(Ia_1)$ or $(Ia_2)$:

$$R_a \diagdown = N \diagdown OR_c \quad (Ia_1)$$

$$\underset{R_a}{\overset{R_b}{\diagdown}} = N \diagdown OR_c \quad (Ia_2)$$

wherein:

$R_a$ is:

[structure: 2-hydroxyphenyl group]

$R_b$, which is identical or different to $R_a$, represents a hydrocarbon group containing 1 to 20 carbon atoms, said hydrocarbon group being:

a linear or branched, saturated or unsaturated, acyclic aliphatic group, a saturated, unsaturated or aromatic, monocyclic or polycyclic, carbocyclic or heterocyclic, group, or a concatenation thereof, and $R_c$ represents a hydrogen atom.

2. The process according to claim 1, wherein the ligand is Salox, or Salox-Me.

3. The process according to claim 1, the amount of ligand is such that the ratio between the number of moles of ligand and the number of moles of metal is of from 2 to 1.

4. The process according to claim 1, wherein the compound carrying a leaving group has the following formula (IV):

$$R_0 - Y \quad (IV)$$

wherein:

Y is a leaving group, and $R_0$ represents a hydrocarbon group containing 2 to 20 carbon atoms having a double bond or a triple bond located in the position a to the leaving group Y, a monocyclic group, a polycyclic group, an aromatic group, a carbocyclic group, or a heterocyclic group.

5. The process according to claim 4, wherein:

$R_0$ represents:

an aliphatic hydrocarbon group containing a double bond or a triple bond in the position a to the leaving group Y, or a cyclic hydrocarbon group containing an unsaturated bond carrying a leaving group, or a monocyclic or polycyclic, carbocyclic or heterocyclic, aromatic group, and Y represents a leaving group being a halogen atom or a sulphonic ester group having the following formula $-OSO_2-R_c$, wherein $R_c$ is a hydrocarbon group.

6. The process according to claim 4, wherein:

Y represents a bromine or chlorine atom or a sulphonic ester group having the following formula $-OSO_2-R_c$, wherein $R_c$ is a linear or branched alkyl group containing 1 to 4 carbon atoms, a phenyl group, a tolyl group or a trifluoromethyl group.

7. The process according to claim 4, wherein the compound carrying a leaving group is selected from the group consisting of the following compounds:

(1) aliphatic compounds having a double bond and having the following formula (IVa):

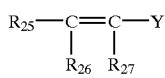

(IVa)

wherein

R$_{25}$, R$_{26}$ and R$_{27}$, which are identical or different, represent a hydrogen atom or a hydrocarbon group containing 1 to 20 carbon atoms, being:
- a linear or branched, saturated or unsaturated, aliphatic group,
- a monocyclic or polycyclic, saturated, unsaturated or aromatic, carbocyclic or heterocyclic, group,
- or a concatenation of aliphatic, carbocyclic or heterocyclic, groups as defined above, and Y represents the leaving group, (2) aliphatic compounds having a triple bond, and having the following formula (IVb):

(IVb)

wherein

R$_{25}$ has the meaning given above, and

Y represents the leaving group as defined above, and (3) aromatic compounds having the following formula (IVc):

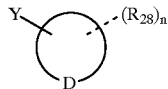

(IVc)

wherein:

D represents a residue of a cycle forming all or a portion of a monocyclic or polycyclic, carbocyclic or heterocyclic, aromatic system, R$_{28}$, which is identical or different, represents a substituent on the cycle, Y represents the leaving group, and n" represents the number of substituents on the cycle.

8. The process according to claim 4, wherein the compound carrying a leaving group is vinyl chloride, vinyl bromide, bromoalkyne, iodoalkyne, β-bromostyrene, β-chlorostyrene, p-chlorotoluene, p-bromoanisole or p-bromotrifluorobenzene.

9. The process according to claim 1, wherein the catalyst comprises at least one metallic element M selected from the group consisting of copper, silver, palladium, cobalt, nickel, iron and zinc.

10. The process according to claim 9, wherein the catalyst is a copper halide catalyst.

11. The process according to claim 1, wherein the reaction is carried out in the presence of a base.

12. The process according to claim 11, wherein the base is:
- an alkali metal carbonate, bicarbonate or hydroxide,
- an alkaline-earth metal carbonate, bicarbonate or hydroxide,
- an alkali metal hydride,
- an alkali metal alcoholate, or
- a tertiary amine.

13. The process according to claim 12, wherein the base is:
- sodium, potassium or caesium carbonate, bicarbonate or hydroxide,
- an calcium, barium or magnesium carbonate, bicarbonate or hydroxide,
- sodium hydride, or
- sodium methylate, ethylate or tertiobutylate.

14. The process according to claim 1, wherein the reaction is carried out in the presence of an organic solvent.

15. The process according to claim 14, wherein the organic solvent is:
- a linear or cyclic carboxamide,
- dimethylsulphoxide (DMSO),
- hexamethylphosphotriamide (HMPT),
- tetramethylurea,
- a nitro compound,
- an aliphatic or aromatic nitrile,
- an organic carbonate,
- an alkyl ester,
- a halogenated aromatic hydrocarbon,
- or a nitrogen-containing heterocycle.

16. The process according to claim 15, wherein the organic solvent is acetonitrile, tetramethylene sulphone, chlorobenzene, toluene, pyridine, picoline or a quinoline.

17. The process according to claim 1, wherein the reaction is carried out at a temperature of from 0° C. to 120° C.

18. The process according to claim 17, wherein the temperature is of from 25° C. to 85° C.

* * * * *